United States Patent [19]

George, Jr.

[11] Patent Number: 5,102,784

[45] Date of Patent: Apr. 7, 1992

[54] RESTRICTION AMPLIFICATION ASSAY

[75] Inventor: Albert L. George, Jr., Gaithersburg, Md.

[73] Assignee: Oncor, Inc., Gaithersburg, Md.

[21] Appl. No.: 519,146

[22] Filed: May 4, 1990

[51] Int. Cl.[5] .................. C12Q 1/68; C12N 9/12; G01N 33/566; G01N 33/48

[52] U.S. Cl. ........................... 435/6; 435/194; 536/26; 536/27; 536/28; 536/29; 436/501; 436/94

[58] Field of Search ............ 435/6, 194; 536/26, 536/27, 28; 436/501, 94; 935/77, 78

[56] References Cited

U.S. PATENT DOCUMENTS

4,725,537 2/1988 Fritsch et al. .................. 435/6

Primary Examiner—Amelia Burgess Yarbrough
Assistant Examiner—Stephanie W. Zitomer
Attorney, Agent, or Firm—Burns, Doane, Swecker & Mathis

[57] ABSTRACT

The present invention relates to a method, reagent and kit for the determination of the presence of target nucleotide sequences by restriction amplification. In the process to detect nucleic acid sequences a target molecule containing a specific restriction site is hybridized with a labeled probe containing a sequence homologous to at least 28 bases of the target molecule. The probe is cleaved with a restriction enzyme that releases the probe for detection if the probe hybridizes to the specific target. A second oligonucleotide is present in the reaction that is homologous to the 3 prime end of the probe molecule and also conains 5 prime base or bases that will reconstitute the restriction enzyme site on the target. Thus, the cleaved probe constantly regenerates and is highly detectable if the target sequence is present in the assay.

103 Claims, 3 Drawing Sheets

Fig.1

```
FIRST
OLIGONUCLEOTIDE:   *-5'ACC ATG GCT GAT CCT GCA GGT ACC AAT G 3'
                                        ↓
HPV-16:            XXX  TGG TAC CGA CTA GGA CGT CCA TGG TTA C XXX
```

HYBRIDIZE
↓

```
          *- ACC ATG GCT GAT CCT GCA GGT ACC AAT G
          XXX TGG TAC CGA CTA GGA CGT CCA TGG TTA C XXX
```

Pst I
↓

```
      *- ACC ATG GCT GAT CCT GCA  +  GGT ACC AAT G

+

XXX TGG TAC CGA CTA GG  +  A CGT CCA TGG TTA C XXX
```

FIRST OLIGO REHYBRIDIZES
WITH TARGET END
↓

```
          *- ACC ATG GCT GAT CCT GCA GGT ACC AAT G
                              A CGT CCA TGG TTA C XXX
```

+

SECOND OLIGONUCLEOTIDE:        5' GGA TCA GCC ATG GT 3'
↓

```
          *- ACC ATG GCT GAT CCT GCA GGT ACC AAT G
          XXX TGG TAC CGA CTA GGA CGT CCA TGG TTA C  XXX
```

\* = DETECTABLE MARKER

Fig. 2

```
FIRST
OLIGONUCLEOTIDE:    *-5'ACC ATG GCT GAT CCT GCA GGT ACC AAT G3'

+

SUBSTRATE:              GTT ATC GCA TAA GGT CGA ATG

+

Pst I

+

SECOND
OLIGONUCLEOTIDE:            GGA TCA GCC ATG GT
                                    │
                                    ▼

*-5'ACC ATG GCT GAT CCT GCA GGT ACC AAT G3'
```

Fig. 3

RESTRICTION AMPLIFICATION ASSAY

BACKGROUND OF THE INVENTION

1. Field of the Invention

The present invention relates to methods, reagents and kits for the determination of the presence of target nucleotide sequences. In particular, the present invention relates to a method for conducting an assay for the presence of a specific target nucleotide sequence in a sample containing an unknown quantity of said specific target nucleotide sequence and to probes for use in such an assay.

2. Description of the Prior Art

In the technology of manipulating genetic material or in evaluating the genetic character of an organism, it is often desirable to ascertain if a particular gene or part of a gene is present in an organism or in an extracellular extract of genetic material from that organism. Since any gene or gene portion is, in essence, a specific sequence of nucleotide bases forming all or part of a polynucleotide molecule, it is possible to directly test the sample polynucleotide to discover if the specific sequence of nucleotide bases forming the gene is present in the sample.

Interest in specific sequences of nucleotide bases may involve detecting the presence of pathogens, determining the presence of alleles, detecting the presence of lesions in a host genome and detecting a particular mRNA or the modification of a cellular host, to name only a few illustrative examples. Genetic diseases such as Huntington chorea, muscular dystrophy, phenylketonuria, thalassemias and sickle cell anemia can be diagnosed by the analysis of an individual's DNA. Furthermore, diagnosis or identification of viruses, viroids, bacteria, fungi, protozoa or any other plant or animal life form can be determined by hybridization assays with nucleotide probes.

Nucleic acid detection assays of various types have been documented in the literature. These types of assays, and in particular those requiring detection of polynucleotides, are based on the purine-pyrimidine base pairing properties of complementary nucleic acid strands in DNA-DNA or DNA-RNA duplexes. This base-pairing process most frequently occurs through formation of hydrogen bonds in the pairing of adenosine-thymine (A-T) and guanosine-cytosine (G-C) bases in double-stranded DNA; adenosine-uracil base pairs may additionally be formed by hydrogen bonding in DNA-RNA hybrid molecules. Base pairing of nucleic acid strands for determination of the presence or absence of a given nucleotide sequence involving sample nucleotide sequences and a probe nucleotide sequence is commonly referred to as nucleic acid hybridization or simply hybridization.

One of the most powerful tools of molecular biology is the ability to fractionate nucleic acids and to determine which nucleic acids have sequences complementary to an array of DNA or RNA molecules. The Southern blot is a well known method for transferring electrophoretically fractioned DNA from a gel matrix to a nitrocellulose solid support by passive diffusion, followed by hybridization to a labeled probe. Similar procedures are used for detecting RNA with minor modifications and this method is known in the art as the Northern blot. The use of dried agarose gels as the immobilized phase is known as the Unblot method. All of these assay techniques are valuable tools for analyzing mRNA's, clones, genes, fragments, flanking sequences, repetitive elements and the like.

U.S. Pat. No. 4,358,535 describes a method for detecting pathogens using a target nucleic acid sequence. The method involves fixing a target nucleic acid sequence to an inert support before hybridization with a radioactively labeled nucleotide probe. The target nucleic acid sequence is then determined by detecting the presence of any label on the inert support.

European Patent Application No. 0 117 440 discloses non-radioactive chemically labeled polynucleotide probes and methods of using the probes. The target nucleic acid sequence is also fixed to a solid support.

U.S. Pat. Nos. 4,767,699 and 4,795,701 disclose a nucleic acid displacement assays. These assays utilize two polynucleotides; one polynucleotide is labeled, and the other polynucleotide is used to displace the labeled probe from the target sequence, thereby allowing detection of the target molecule. These assays use ATP to detect whether hybridization has occurred with the target molecule.

Many of the assays using nucleotide probes have problems in the detection systems. Sensitivity of the labeled probe and background levels that are generated during the assay often lead to erroneous results.

To facilitate more efficient detection of a nucleic acid sequence from a given sequence of DNA or RNA a target amplification method may be utilized. This method, known as PCR, is described in U.S. Pat. No, 4,683,195 and uses a set of primers and a DNA polymerase to extend the nucleic acid sequence of the target nucleotide and amplify it for future probe detection. By amplifying the DNA sequence, the target nucleotide can be more efficiently detected with the nucleotide probe. One of the problems encountered in this probe assay is contamination of the reaction medium.

Type II restriction enzymes are known in the art for making double-stranded scissions at specific sites within a DNA molecule. These enzymes are prevalent in bacteria, contain only one type of subunit and $Mg^{2+}$ alone is required for DNA cleavage. DNA cleavage or scission occurs at specific sites within or adjacent to the enzyme's recognition site. More than 400 restriction enzymes have been isolated from bacterial strains to date. These restriction enzymes have been characterized primarily with respect to their recognition sequences and cleavage specificity. The majority of restriction enzymes or endonucleases recognize sequences 4-6 nucleotides in length, but some have been found with 7-8 base recognition sites. Most, but not all, recognition sites contain a dyad axis of symmetry and in most cases all the bases within the site are uniquely specified. Recognition of the symmetrical sequence of the hybridized sequences or palindromes is made by endonucleases. Endonucleases with symmetrical recognition sites generally cleave symmetrically.

The use of restriction enzymes with their specific cleavage sites is well recognized in the art. Usually restriction enzymes are used for the specific mapping, cloning and characterization of DNA sequences. However, they have been used in various nucleotide probe assays. For instance, U.S. Pat. No. 4,683,194 discloses a method for detecting the presence or absence of a specific restriction site in a nucleic acid sequence by hybridization with a nucleic acid probe that is complementary to one strand of the nucleic acid sequence spanning the restriction site. The hybridized sequence is then cleaved with a restriction enzyme and the resulting cut and uncut oligomers are separated and detected based on the type of probe label.

A similar concept for detecting a target nucleotide having a half-restriction site is set forth in U.S. Pat. No. 4,725,537. This patent discloses the use of a restriction endonuclease in a displacement-type of assay.

Another type of assay that uses the concept of cleaving a nucleic acid sequence in a nucleotide probe is disclosed in U.S. Pat. No. 4,876,187. This method is used to detect DNA or RNA sequences by specifically cleaving the nucleic acid sequence of the probe at in least one point thereby removing any reporter molecules not bound to a complementary target DNA sequence. This assay improves the signal to noise ratio of the detection system and is a highly sensitive assay.

Although the aforementioned assays do provide a method for detecting nucleic acid sequences in a target molecule, the need still exists for an assay system that provides very high sensitivity, ease of detection, less contamination in the assay medium and ease of operation, while avoiding false positive results.

The present invention overcomes the disadvantages associated with the techniques discussed above by introducing a highly sensitive detection method for detecting a nucleic acid sequence through the use of a novel form of restriction amplification. A second oligonucleotide is present in the assay to recycle the cleaved target sequence of interest thereby amplifying the labelled and cleaved probe oligonucleotide.

SUMMARY OF THE INVENTION

Accordingly, an object of the present invention is provide a highly sensitive nucleic acid recycling or probe amplification assay for detecting a nucleic acid sequence.

Another object of the present invention is to provide an assay that recycles the target sequence of interest and thereby amplifies the labeled probe.

The present invention provides a method for detecting the presence of a nucleic acid sequence in a biological sample, said method comprising the steps of:

(a) providing a first oligonucleotide which comprises a nucleic acid sequence and a scissile linkage that is substantially complementary to a nucleic acid target sequence, said first oligonucleotide having a detectable marker attached thereto;

(b) adding a second oligonucleotide to form a mixture that is substantially complementary to an end of the first oligonucleotide that does not rehybridize to the target sequence and comprising at least one base that will reconstitute the cleaved scissile linkage on a target molecule;

(c) adding a cleaving enzyme to said reaction mixture which is able to cleave the scissile linkage if said target sequence and said first oligonucleotide hybridize;

(d) hybridizing said reaction mixture; and (e) detecting the cleaved detectable marker.

Another embodiment of the present invention recites:

A method of detecting in a sample the presence of a nucleic acid sequence, said method comprising the steps of:

(a) denaturing a target nucleic acid sequence containing a scissile linkage in the presence of:

(i) a first oligonucleotide which contains a scissile linkage and is substantially complementary to the nucleic acid sequence of the target molecule; (ii) a second oligonucleotide that is substantially complementary to the 3 prime end of said first oligonucleotide and comprises a 5 prime base or bases that will reconstitute the cleaved scissile linkage on said target molecule to form a mixture;

(b) adding a cleaving enzyme to said mixture;

(c) permitting said reaction mixture to hybridize whereby the cleaving enzyme will release the detectable marker from said first oligonucleotide sequence; and (d) detecting the cleaved detectable marker.

Still another embodiment of the present invention recites:

A method for detecting the presence of a nucleic acid sequence in a biological sample, said method comprising the steps of:

(a) hybridizing a target molecule having a scissile linkage to a labelled first oligonucleotide probe that has a complementary sequence to said target and a detectable marker to provide a probe:target duplex;

(b) cleaving said duplex at the scissile linkage;

(c) adding a second oligonucleotide that reconstitutes the cleaved scissile linkage on the target molecule;

(d) recycling the reconstituted target molecule; and (e) detecting said cleaved first oligonucleotide probe.

Yet another object of the presence invention is to provide kits for diagnosis of various diseases using the above-described method.

DETAILED DESCRIPTION OF THE PREFERRED EMBODIMENTS OF THE INVENTION

More particularly, the present invention relates to a method for detecting nucleic acid sequences of interest in a target molecule. This assay uses a second oligonucleotide that is able to reconstitute the scissile linkage of said target molecule, permitting cleavage of the first oligonucleotide, thereby recycling the target sequence and amplifying the amount of the cleaved first oligonucleotide probe.

The term "oligonucleotide" as used herein refers to a compound made up of the condensation of a small number of nucleotides. The exact size of the oligonucleotide will depend on many factors including the ultimate function of the use of the oligonucleotide.

As used herein, the term "scissile linkage" refers to a site-specific recognition nucleotide sequence that is cleavable by the use of restriction enzymes or restriction endonucleases.

As used herein, the terms "restriction endonucleases" and "restriction enzymes" refer to bacterial enzymes each of which cut double-stranded DNA at or near a specific recognition nucleotide site.

The sample nucleic acid which may be employed herein may be derived from any source(s), including organisms, provided that it contain the particular restriction site of interest within a given nucleic acid sequence. Thus, the process may employ pure DNA which is single or double stranded or a cDNA or a mixture of nucleic acids, provided they can be cut by restriction endonucleases. Sources include, for example, plasmids such as pBR322, cloned DNA, genomic DNA from any source. Typical sources can be from biological samples including bacteria, yeasts, viruses, and higher organisms such as plants, birds, reptiles and mammals.

Genomic DNA may be prepared from blood, urine, tissue material such as chorionic villi or amniotic cells by a variety of techniques (such as those described by Maniatis et al., in *Molecular Cloning*, (1982) 280-281). If necessary or desired to lower the viscosity, the sample of prepared human DNA to be analyzed may be physically sheared or digested using a specific restriction endonuclease.

The first oligonucleotide used in the present invention is a single-stranded oligonucleotide and has a structure complementary to the nucleic acid sequence being detected. The probe is usually DNA and may contain an unlimited number of bases. However, it is preferable that the probe contains up to about 100 bases, more preferably between about 10 to 40 bases. The probe may be obtained from messenger RNA, from a complementary strand of cDNA obtained by reverse transcription of messenger RNA with reverse transcriptase or by cleavage of the genome, conveniently by endonuclease digestion, followed by cloning of the gene or gene fragment in accordance with known techniques. See, for example, Kornberg, DNA Replication, W. H. Freeman and Co., San Francisco, 1980, pp. 670-679; So et al., *Infect. Immun.*, 21:405-411, 1978. After isolation and characterization of the desired gene or DNA fragment, the gene or DNA fragment may be used for preparation of the probe. The probe may also be chemically synthesized using an automated synthesizer such as a MILLI-GEN ® synthesizer. Chemical synthesis of the probes is the preferred method to obtain the desired probe for use in the present invention.

For the most part, the oligonucleotide probe will be labeled with a detectable marker using an atom, an inorganic radical, radionucleotide, heavy metal, antibody, enzyme and the like. Conveniently, a radioactive label may be employed. Radioactive labels include $^{32}P$, $^{3}H$, $^{14}C$ and the like. Any radioactive label may be employed which provides for an adequate signal and has sufficient half-life. Other labels include ligands, which can serve as a specific binding pair member to a labeled antibody, fluorescers, chemiluminescers, enzymes, antibodies which can serve as a specific binding pair member for a labeled ligand and the like. A wide variety of labels have been employed in immunoassays which can be readily employed in the present assay. The choice of label will be governed by the effect of the label on the rate of hybridization and binding of the probe to the genetic DNA. It will be necessary that the label provide sufficient sensitivity to detect the amount of DNA available for hybridization. Other considerations include ease of synthesis of the probe, readily available instrumentation, the ability to automate, convenience and the like.

The manner in which the label is bound to the probe will vary depending upon the nature of the label. For a radioactive label, a wide variety of techniques can be employed. Commonly employed is end labeling with an $\alpha$-$^{32}$P-NTP and T4 polynucleotide kinase. Alternatively, nucleotides can be synthesized where one or more of the elements present are replaced with a radioactive isotope, e.g., hydrogen with tritium.

Where other radionucleotide labels are involved, various linking groups can be employed. A terminal hydroxyl can be esterified with inorganic acids. For example, $^{32}P$ phosphate or $^{14}C$ organic acids can be esterified via the terminal hydroxy or esterified to provide linking groups to the label. Alternatively, intermediate bases may be substituted with activatable linking groups which can be linked to the label.

Ligands and antiligands may be varied widely. Where a ligand has a natural receptor such as biotin, thyroxine and cortisol, the ligand can be used in conjunction with labelled naturally occurring receptors. Any compound can be used, either haptenic or antigenic, in combination with an antibody.

Enzymes of interest as labels will primarily be hydrolases, particularly esterases and glycosidases, phosphatases, or oxidoreductases, particularly peroxidases. Fluorescent compounds include fluorescein and its derivatives, rhodamine and its derivatives, dansyl, umbelliferone and the like. Chemiluminescers include luciferin and 2,3-dihydrophthalazinediones, i.e., luminol.

Yet another method for labeling and detecting the nucleotide probe is disclosed in U.S. Pat. No. 4,868,103, in which an energy transfer results in the generation of bathochromic and/or delayed fluorescence emission. Fluorescence radiation, emitted from a first energy emitter ($E_1$) is absorbed by a second energy emitter ($E_2$). The second emitter emits fluorescence radiation of a longer wavelength than the first energy emitter. ($E_1$) and ($E_2$) must be within a proximate distance of each other so that the energy emitted by ($E_1$) can be absorbed by ($E_2$) and ($E_2$) emits fluorescent energy at a longer wavelength.

Any means for labeling and detecting the labeled probe can be used in the present invention. It is preferable, however, that the label is bound at a distance away from the scissile linkage and is situated at the 3 prime or 5 prime end of the first probe oligonucleotide.

Besides having a label on the first oligonucleotide the first oligonucleotide must also contain a scissile linkage that is complementary to the target molecule of interest. The scissile linkage must be readily cleavable by restriction enzymes or other means after hybridization has occurred. When the first oligonucleotide is a DNA sequence, the linkage may be cleaved by restriction enzymes.

The restriction enzymes are well known in the art and have specific recognition sites. There are more than 400 different restriction endonucleases which can be isolated from bacteria and the present invention contemplates the use of any of these enzymes. The criteria for choosing the restriction enzyme is based upon the recognition site of the target nucleotide molecule, the first oligonucleotide probe, and the properties of the enzyme. The first oligonucleotide probe containing the scissile linkage must be complementary to the target nucleotide's recognition or scissile linkage site which upon hybridization of these oligonucleotides and addition of the restriction enzyme, the duplex will be cleaved.

Restriction enzymes or endonucleases are relatively stable proteins. Their purification to homogeneity is often not necessary. All restriction enzymes require a cofactor for cleavage such as $Mg^{2+}$ or $Mn^{2+}$ and are most active in the pH range of 7.2 to 7.6. Typically for enzyme cleavage an appropriate buffer system is used. These buffer systems vary among the restriction enzymes used to cleave a hybridized duplex. Therefore, in addition to the DNA substrate and restriction enzyme, most reaction solutions will contain TRIS buffer tris(-hydroxymethyl)aminomethane, $Mg^{2+}$, NaCl, 2-mercaptoethanol and bovine serum albumin (BSA). The predominant difference among the restriction enzymes is their dependence on ionic strength. To maximize cleavage efficiencies the buffering systems are varied among the restriction enzymes. For instance, if a Hind III restriction enzyme is used in the assay, a buffer containing 50 mM NaCl, 25 mM TRIS-HCl, pH 7.7, 10 mM $MgCl_2$, 10 mM β-mercaptoethanol and 100 μg/ml BSA is used to maximize the cleavage efficiency. If an Eco RI enzyme is used the buffering system contains 50 mM NaCl, 100 mM TRIS-HCl, pH 7.5, 5 mM $MgCl_2$ and 100 μg/ml BSA. Therefore, the present invention contemplates the use of different buffering systems, which vary according to the restriction enzyme used in the assay.

Restriction enzymes may also vary in temperature optima. Most cleavages are performed at 37° C., but a few endonucleases such as Sma I prefer lower incubation temperatures, and several, mainly those isolated from thermophiles such as Taq I, require much higher temperatures. Therefore, the reaction temperature in the present invention is chosen taking into consideration the restriction enzyme used in the assay.

Besides cleaving the double-stranded molecule formed after hybridization with restriction enzymes, any other method available can be used in the cleavage process. For instance, certain chemicals may be used to cleave double-stranded complexes at specific sites.

The present invention also uses a second oligonucleotide which reconstitutes with the cleaved target molecule of interest such that hybridization with the probe oligonucleotide occurs within the assay. The second oligonucleotide acts to recycle the target sequence of interest and thereby amplifies the amount of cleaved probe for detection purposes. This second oligonucleotide is a single-stranded nucleotide that is complementary to an end of the first probe oligonucleotide such as the 3 prime end or 5 prime end. The second oligonucleotide may be derived via processes similar to the synthesis of the first oligonucleotide, as described above.

Figure 1:
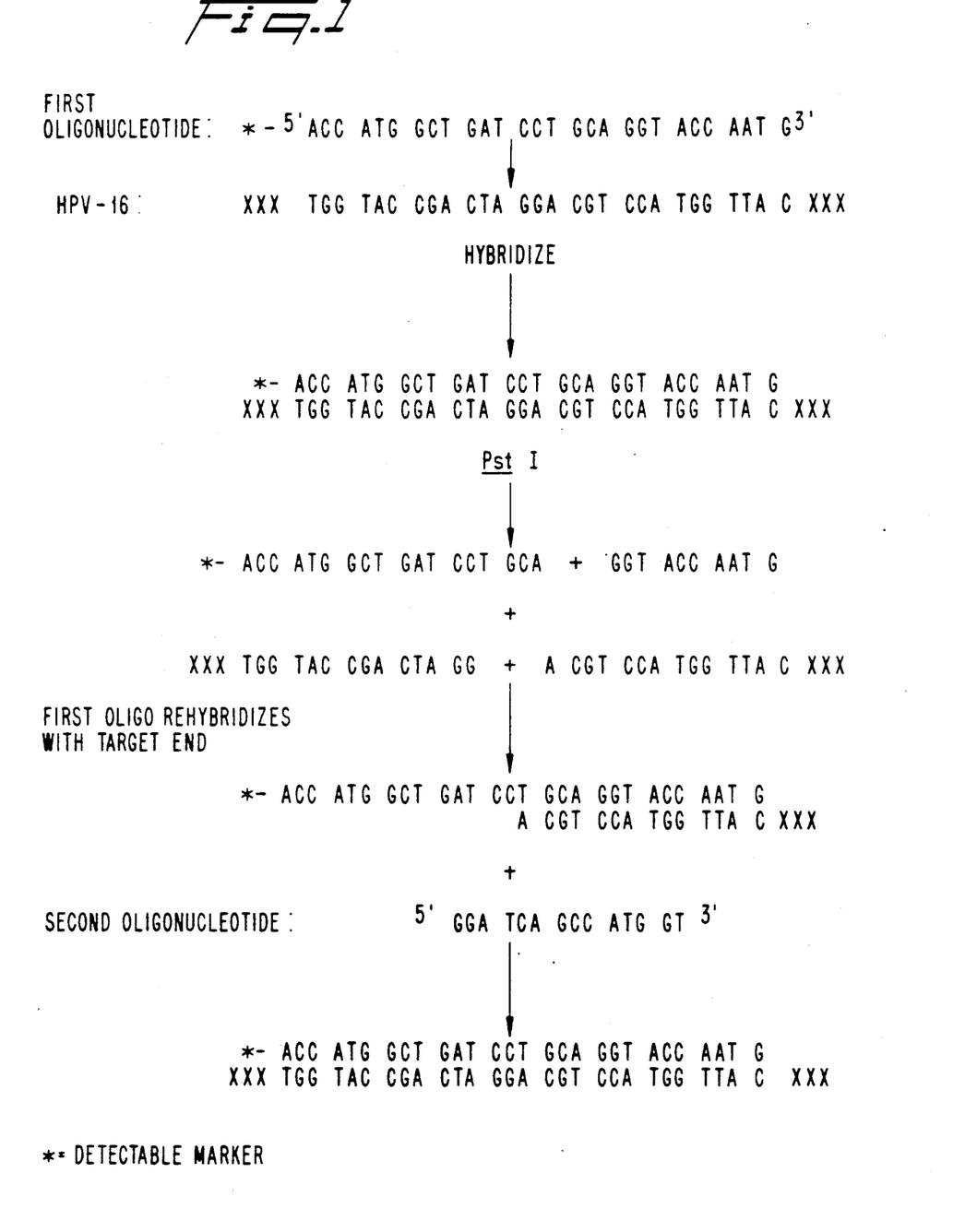
FIG. 1 is a schematic representation of the method of the present invention with a complementary target sequence.
Figure 2:
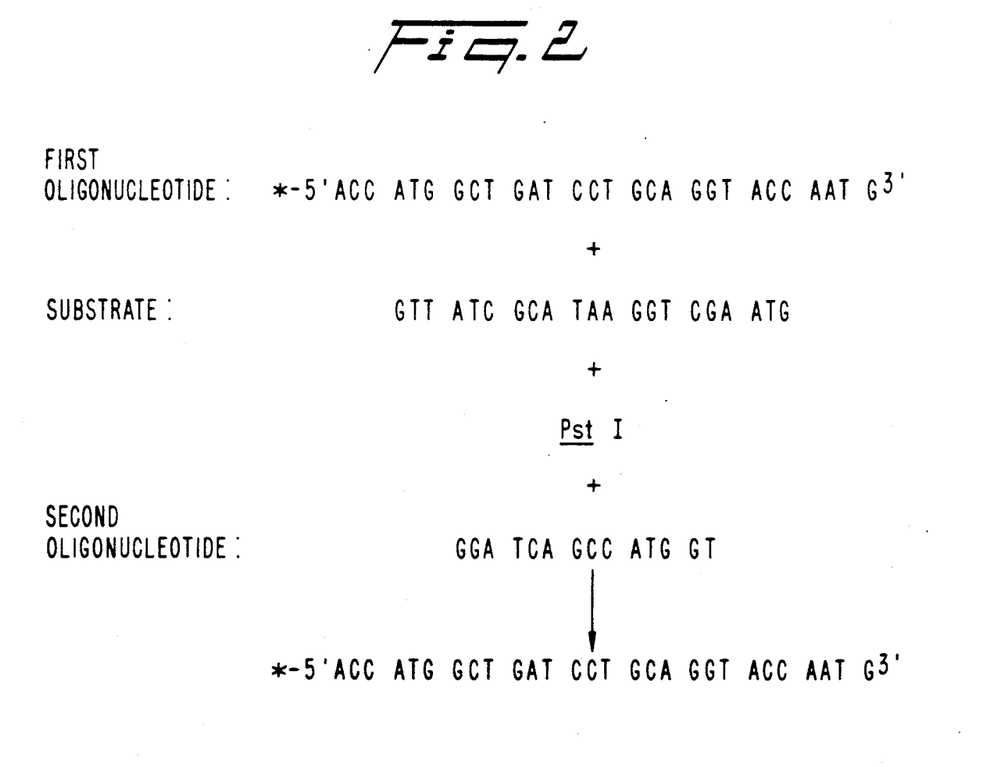
FIG. 2 is a schematic representation of the method of the present invention with a non-complementary non-target sequence.

Besides being complementary to the 3 prime or 5 prime end of the first oligonucleotide, the second oligonucleotide should contain bases such as a 5 prime base or 3 prime base, that will reconstitute the target molecule at the site that was cleaved by the restriction enzyme. After reconstituting with the cleaved end of the target molecule, hybridization once again occurs with the first labeled oligonucleotide and the process "cycles" once again and releases the labeled probe into the reaction media. The second oligonucleotide may contain up to 100 bases, preferably between about 10 to 20 bases, more preferably about 14 bases. FIGS. 1 and 2 are illustrative examples of how the present invention works.

The assay is initiated by denaturing the sample target molecule to form a single-stranded molecule. The denaturation of the target molecule or substrate is generally performed by boiling. In addition, the substrate, first oligonucleotide, second oligonucleotide buffer and distilled water may be mixed together and boiled for 5 to 10 minutes. The mixture is then allowed to cool to room temperature. After cooling, the restriction enzyme may then be added to initiate the reaction.

The temperature at which the assay is run may vary according to the restriction enzyme used, the length of the oligonucleotide probe and the G+C content of the oligonucleotides present in the assay. Suggs et al, in "Developmental Biology Using Purified Genes," (D. D. Brown, ed.), p.683. Academic Press, New York, 1981., developed an empirical formula to determine the appropriate hybridization temperature based on the temperature at which an oligonucleotide DNA complex is dissociated. The formula derived was: $T_d = 2°$ (number of A+T residues)+4°(number of G+C residues). This empirical formula can be used to estimate the reaction temperature, but one must also take into account the restriction enzyme used in the assay. As discussed above, many restriction enzymes are active at 37° C., but others may require higher or lower temperatures. The temperature of the reaction is chosen such that optimal rates of hybridization, as well as cleavage of the restriction enzyme occurs.

The reaction time may vary depending upon the concentration of the sequence of interest, the stringency, the length of the complementary first oligonucleotide probe sequence, the restriction enzyme used and the like. Enough time should be provided to permit amplification of the probe by recycling the target sequence of interest. Usually the assay is run from 1 to 3 hours, more preferably for two hours.

After the reaction has run, it is stopped by placing an aliquot of the reaction mixture into a polyacrylamide gel loading buffer. The sample is then electrophoresed and an autoradiograph is taken of the electrophoresed gel. One can then proceed to quantitate the amount of probe generated on a scanning densitometer, if desired.

In order to further illustrate the present invention and the advantages thereof, the following specific examples are given it being understood that same are intended as illustrative and in nowise limitative.

Synthesis of Oligonucleotides

Two oligonucleotides are required for the restriction amplification process. The synthesis of the first oligonucleotide having the sequence 5'ACC ATG GCT GAT CCT GCA GGT ACC AAT G3' (28 mer) and the second oligonucleotide having the sequence 5'GGA TCA GCC ATG GT3' (14 mer) were prepared by phosphoramidite chemistry and were subsequently purified by anion exchange HPLC. The oligonucleotides synthesized by the phosphoramidite approach contained a free 5'-OH.

Labeling of First Oligonucleotide

The first oligonucleotide contained a 5'-OH group which was labeled by transfer of the [$^{32}$P]phosphate from [γ$^{32}$P]ATP using polynucleotide kinase. The labeling reaction was carried out by dissolving each oligonucleotide in distilled water. The concentration of each oligonucleotide dissolved in the water was $0.5 \times 10^{-11}$ molar. The reaction was performed using 1 μl of the first oligonucleotide ($0.5 \times 10^{-11}$ molar), 5 μl of kinase buffer which contained 0.5 M TRIS-HCl at pH 7.6, 1 mM spermidine, 50 mM dithiothreitol, 1 mM EDTA and 0.1 M $MgCl_2$, 30.5 ml distilled water, 12.5 μl $^{32}$P-ATP (0.125 millicuries or 3000 curies/μmole) and 1 μl of polynucleotide kinase (10 units). The above-mentioned reaction ingredients were combined and incubated at 37° C. for 1 hour. The reaction was terminated by heating the reacted mixture to 80° C. for 10 minutes.

The labeled first oligonucleotide prepared by this method is stable for at least one week when stored at −20° C.

HPV 16 Substrate

The HPV16-DNA virus was isolated from a cervical lesion by methods known in the art and cloned into pBR322 using standard techniques. The cloned DNA was isolated by a modified procedure described by H. C. Birnboim and J. Daly, *Nucleic Acids Res.*, 7, 1513 (1979).

The cells were grown overnight in 5 ml of LB broth containing 100 μg/ml ampicillin at 37° C. with vigorous shaking. 1.5 ml of the culture was transferred to a 1.5 ml centrifuge tube and centrifuged at 10,000 g for 1 minute. The supernatant was then carefully removed leaving the pellet as dry as possible. The cells were resuspended by vortexing in 100 μl of an ice-cold solution containing 50 mM glucose, 10 mM EDTA and 25 mM TRIS-HCl at pH 8.0. The resuspended cells were allowed to incubate for 5 minutes at room temperature. 20 μl of a freshly prepared solution containing 0.2 N NaOH, 1% sodium dodecyl sulfate (SDS) was added to the cells and mixed by inversion. The cells were further incubated for 5 minutes at 0° C.

After incubation, 150 μl of ice-cold potassium acetate at pH 4–8 (prepared by adding 11.5 ml glacial acetic acid and 28.5 ml of water to 60 ml of 5 M potassium acetate) was added and the mixture was inverted for 10 seconds and incubated at 0° C. for 5 minutes.

The mixture was then centrifuged for 5 minutes at 10,000 g, and the supernatant was transferred to another tube. The supernatant was centrifuged again at 10,000 g for 5 minutes, and the supernatant was transferred to another fresh test tube. RNase A was then added to the supernatant, having a final concentration of 20 μg/ml. The reaction was incubated at 37° C. for 20 minutes.

After incubation, an equal volume of phenol: chloroform (1:1, saturated with 50 mM TRIS-HCl at pH 8.0, 100 mM NaCl, 1 mM EDTA) was added and the mixture was vortexes for 30 seconds and centrifuged at 10,000 g for 30 seconds. The aqueous phase was then transferred to a fresh test tube.

2.5 volumes of ethanol was then added to the aqueous phase and mixed. The mixture was incubated at −70° C. for 5 minutes. The mixture was centrifuged at 10,000 g for 5 minutes and the supernatant was removed. The pellet was then rinsed by adding 1 ml of prechilled 70% ethanol and mixed briefly. The mixture was then centrifuged for 1 minute. The supernatant was then removed, and the pellet was dried under vacuum.

The DNA obtained from this procedure was dissolved in 20 μl of deionized water.

Restriction Amplification Assay

The restriction amplification assay was initiated by combining the HPV 16 substrate, the first oligonucleotide labeled probe, the first unlabeled oligonucleotide, a PST I buffer, and deionized water. In this RAMP assay two controls were simultaneously run with the samples. Two different temperatures of 32° C. and 37° C. were utilized in this example.

Stock solutions of the reaction components were first prepared. The oligonucleotides were diluted to $0.5 \times 10^{-11}$ molar solutions. Similarly, the second oligonucleotide was also diluted to create a $0.5 \times 10^{-11}$ stock solution. The HPV16 stock was diluted with distilled water to form a 100 μg/ml stock solution. The Pst I restriction enzyme stock solution contained 50 units/μl.

A specific aliquot was taken from these stock solutions for each assay. The total reaction volume was 50 μl. Each reaction assay contained 1 μl (100 μg) of HPV16, 2 μl of the labeled first oligonucleotide, 2 μl of unlabeled first oligonucleotide, 4 μl of the second oligonucleotide, 5 μl of Pst I buffer containing 100 mM NaCl, 10 mM TRIS-HCl at pH 7.7, 10 mM MgCl$_2$, 1 mM DTT and 100 μg/ml BSA. 5 μl of Pst I was used. Distilled water was added in varying quantities such that the final volume in each assay tube was equal to 50 μl.

Five assays were run in separate tubes. The first tube (#1) contained 2 μl of the first oligonucleotide labeled with $^{32}$P, 2 μl of cold unlabeled first oligonucleotide, 4 μl of the second oligonucleotide, 5 μl Pst I buffer and 32 μl distilled water. No HPV-16 was added to the first assay mixture.

The second assay tube (#2) contained 1 μl (100 μg) HPV-16, 2 μl of the first oligonucleotide labeled with $^{32}$P, 2 μl of cold unlabeled first nucleotide, 4 μl of the second oligonucleotide, 5 μl of Pst I buffer and 31 μl of distilled water.

The third assay tube (#3) contained 1 μl of HPV-16 (100 μg), 2 μl of the first $^{32}$P oligonucleotide, 2 μl of cold first oligonucleotide, 5 ml of Pst I buffer, and 35 μl of distilled water.

The fourth assay tube (#4) contained 1 μl of HPV-16 (100 μg), 2 μl of the first $^{32}$P oligonucleotide, 2 μl of cold unlabelled first oligonucleotide, 5 μl of Pst I buffer, and 35 μl of distilled water.

The fifth assay tube (#5) contained 1 μl of HPV-16 (100 μg), 2 μl of labelled $^{32}$P first oligonucleotide, 2 μl of cold unlabelled first oligonucleotide, 4 μl of second oligonucleotide, 5 μl of Pst I buffer, and 31 μl of distilled water.

Prior to addition of Pst I, the five assay tubes described above were boiled for 5 to 10 minutes and then cooled at room temperature for approximately 10 minutes.

After cooling the samples, the samples were placed in an incubator; assay tube numbers 1, 4, and 5 discussed above were incubated at 37° C. Assay tubes numbers 2 and 3 were incubated at 32° C. To initiate the assay, 5 μl of Pst I enzyme was added to each assay tube. The assay was run for 2 hours.

After incubation, the reaction was stopped by adding 10 μl of a solution containing 80% formamide, 15 mM TRIS-HCl at pH 7.6, 1 mM EDTA, 0.1% w/v bromophenol blue and 0.1% w/v xylene cyanole FF to each assay tube. Each tube was then heated for 5 minutes at 65° C. and cooled rapidly.

Polyacrylamide gels were prepared by making a stock solution containing 30% acrylamide (19:1 acrylamide:bis), 19 grams of acrylamide, 1 gram of N,N'-methylenebisacrylamide and enough deionized water to dilute the solution to 67 ml total volume. A concentrated solution of TBE buffer was prepared by diluting to 1 liter, 108 grams of TRIS base, 55 grams of boric acid and 9.3 grams of Disodium EDTA·2H$_2$O. The pH of the concentrated TBE buffer should be adjusted to 8.3, if appropriate. 48 grams of ultra-pure grade urea (8 M) was added to the stock solution containing the 30% acrylamide. 10 ml of TBE buffer was added and the urea was dissolved in this solution. 50 μl (per 100 ml of acrylamide solution) of N,N,N',N'-tetramethylethylenediamine(TEMED) and 1 ml (per 100 ml) of 10% ammonium persulfate was added and the solution was mixed well. The gel was poured between two glass plates into the electrophoresis apparatus and the comb was inserted immediately.

20 μl of each sample was loaded into the polymerized gel and a running buffer was added that contained 0.089 M TRIS-borate, pH 8.3 and 0.025 M Disodium EDTA. The samples were electrophoresed at 80 volts for 4 hours.

The gels were then wrapped in a plastic folder placed next to Kodak X-OMAT AR film and exposed for 10 minutes.

Figure 3:
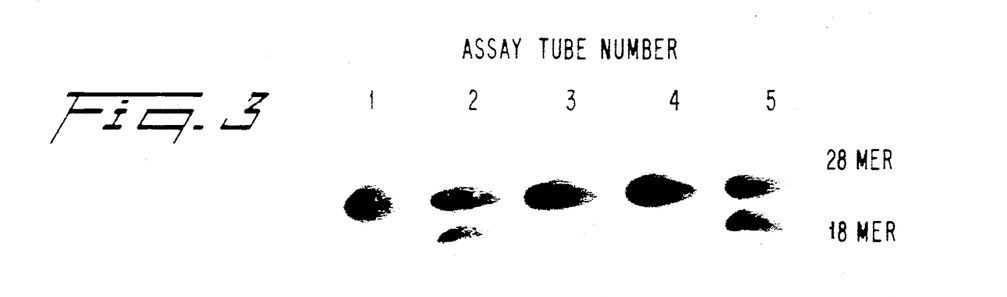
FIG. 3 is an autoradiograph of several samples run using the present assay.

FIG. 3 is an illustrative example of the autoradiograph of the present invention. From the autoradiograph, one can easily determine the formation of the substrate by the presence of the 28 mer oligonucleotide band and the 14 mer oligonucleotide band. Lanes 2 and 5 illustrate a doublet pattern when the substrate is present in the reaction media at two different temperatures. Lanes 3 and 4 are indicative of the presence of only the labeled first oligonucleotides without the second oligonucleotide used to recycle the substrate. Lane 1 is indicative of the pattern obtained when both of the first and second oligonucleotides are present in the assay mixture, but no substrate (i.e., HPV-16) was present in the reaction.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for detecting the presence of a nucleic acid sequence which contains a scissile linkage that is cleavable by a cleaving enzyme in a biological sample, said method comprising the steps of:
   (a) providing a first oligonucleotide which comprises a nucleic acid sequence and a scissile linkage and is substantially complementary to a nucleic acid target sequence, said first oligonucleotide having a detectable marker attached thereto;
   (b) adding to form a mixture a second oligonucleotide that is substantially complementary to an end of the first oligonucleotide and comprises at least one base that will reconstitute the cleaved scissile linkage on a target molecule;
   (c) adding a cleaving enzyme to said reaction mixture which is able to cleave the scissile linkage if said target sequence and said first oligonucleotide hybridize;
   (d) hybridizing said reaction mixture; and
   (e) detecting the cleaved detectable marker in the presence of the first uncleaved oligonucleotide having a detectable marker attached thereto.

2. The method according to claim 1, wherein said target molecule comprises a single-stranded DNA sequence.

3. The method according to claim 2, wherein said first oligonucleotide comprises a single-stranded DNA sequence.

4. The method according to claim 2, wherein said second oligonucleotide comprises a single-stranded DNA sequence.

5. The method according to claim 1, wherein said cleaving enzyme is a restriction enzyme.

6. The method according to claim 1, wherein said target molecule is single-stranded or double-stranded.

7. The method according to claim 1, wherein said hybridization is carried out at a temperature to enhance the efficiency of said cleaving enzyme and the hybridization of the oligonucleotides.

8. The method according to claim 7, wherein said hybridization is carried out at 37° C.

9. The method according to claim 7, wherein said hybridization is carried out at 32° C.

10. The method according to claim 7, wherein said hybridization is carried out between 1 to 4 hours.

11. The method according to claim 10, wherein said hybridization is carried out for about 2 hours.

12. The method according to claim 1, wherein said reaction mixture further comprises a buffering system.

13. The method according to claim 12, wherein said buffering system comprises a $MgCl_2$, NaCl, tris(hydroxymethyl)aminomethane-hydrochloride (TRIS-HCl), dithiothreitol (DTT) and bovine standard albumin (BSA).

14. The method according to claim 13, wherein said buffering system comprises 100 mM NaCl, 10 mM tris(hydroxymethyl)aminomethane-hydrochloride (TRIS-HCl), pH7.7, 10 mM $MgCl_2$, 1 mM DTT and 100 μg/ml BSA.

15. The method according to claim 1, wherein said detectable marker in said first oligonucleotide is a radioactive marker.

16. The method according to claim 15, wherein said radioactive marker is selected from the group consisting of $^{32}P$, $^{3}H$, $^{14}C$ and $^{35}S$.

17. The method according to claim 16, wherein said radioactive marker is $^{32}P$.

18. The method according to claim 1, wherein said detectable marker in said first oligonucleotide is an enzyme marker.

19. The method according to claim 1, wherein said detectable marker in said first oligonucleotide is a ligand which can serve as a specific binding pair member to a labeled compound selected from the group consisting of an antibody, fluorescer, chemiluminescer, enzymes, biotin and mixtures thereof.

20. The method according to claim 1, wherein said first oligonucleotide is up to 100 mer.

21. The method according to claim 20, wherein said first oligonucleotide is between about 10 mer to 40 mer.

22. The method according to claim 21, wherein said first oligonucleotide is about 28 mer.

23. The method according to claim 1, wherein said second oligonucleotide is up to 100 mer.

24. The method according to claim 23, wherein said second oligonucleotide is between about 10 mer to 20 mer.

25. The method according to claim 24, wherein said second oligonucleotide is about 14 mer.

26. The method according to claim 1, further comprising the step of adding to said hybridization reaction mixture a terminating solution.

27. The method according to claim 26, wherein said terminating solution comprises 80% formamide, 15 mM tris(hydroxymethyl)aminomethane-hydrochloride (TRIS-HCl), pH 7.6, 1 mM EDTA, 0.1% w/v bromophenol blue and 0.1% w/v xylene cyanole FF.

28. The method according to claim 27, wherein 100 μl of said terminating solution is added to said reaction mixture.

29. The method according to claim 2, wherein said nucleic acid target sequence is HPV 16.

30. The method according to claim 1, Wherein said detecting step (e) comprises electrophoresing said reaction mixture and autoradiographing said electrophoresed reaction mixture.

31. A method of detecting in a sample the presence of a nucleic acid sequence which contains a scissile linkage that is cleavable by a cleaving enzyme, said method comprising the steps of:
(a) forming a reaction mixture by denaturing a target nucleic acid sequence containing a scissile linkage in the presence of: (i) a first oligonucleotide which contains a scissile linkage and is substantially complementary to the nucleic acid sequence of the target molecule; (ii) a second oligonucleotide that is substantially complementary to an end of said first oligonucleotide and comprises a 5 prime base or bases that will reconstitute the cleaved scissile linkage on said target molecule;
(b) adding a cleaving enzyme to said denatured mixture;
(c) permitting said reaction mixture to hybridize whereby the cleaving enzyme will release the detectable marker from said first oligonucleotide sequence; and
(d) detecting the cleaved detectable marker.

32. The method according to claim 31, wherein said target molecule comprises a single-stranded or double-stranded DNA sequence.

33. The method according to claim 32, wherein said first oligonucleotide comprises a single-stranded DNA sequence.

34. The method according to claim 32, wherein said second oligonucleotide comprises a single-stranded DNA sequence.

35. The method according to claim 31, wherein said cleaving enzyme is a restriction enzyme.

36. The method according to claim 31, wherein said target molecule is single-stranded.

37. The method according to claim 31, wherein said hybridization is carried out at a temperature to enhance the efficiency of said cleaving enzyme and the hybridization of the oligonucleotides.

38. The method according to claim 37, wherein said hybridization is carried out at 37° C.

39. The method according to claim 37, wherein said hybridization is carried out at 32° C.

40. The method according to claim 37, wherein said hybridization is carried out between 1 to 4 hours.

41. The method according to claim 40, wherein said hybridization is carried out for about 2 hours.

42. The method according to claim 31, wherein said reaction mixture further comprises a buffering system.

43. The method according to claim 42, wherein said buffering system comprises a $MgCl_2$, NaCl, tris(hydroxymethyl)aminomethane-hydrochloride (TRIS-HCl), dithiothreitol (DTT) and bovine standard albumin (BSA).

44. The method according to claim 43, wherein said buffering system comprises 100 mM NaCl, 10 mM tris(-hydroxymethyl)aminomethane-hydrochloride (TRIS-HCl), pH7.7, 10 mM $MgCl_2$, 1 mM DTT and 100 μg/ml BSA.

45. The method according to claim 31, wherein said detectable marker in said first oligonucleotide is a radioactive marker.

46. The method according to claim 45, wherein said radioactive marker is selected from the group consisting of $^{32}P$, $^{3}H$, $^{14}C$ and $^{35}S$.

47. The method according to claim 46, wherein said radioactive marker is $^{32}P$.

48. The method according to claim 31, wherein said detectable marker in said first oligonucleotide is an enzyme marker.

49. The method according to claim 31, wherein said detectable marker in said first oligonucleotide is a ligand which can serve as a specific binding pair member to a labeled compound selected from the group consisting of an antibody, fluorescer, chemiluminescer, enzymes, biotin and mixtures thereof.

50. The method according to claim 31, wherein said first oligonucleotide is up to 100 mer.

51. The method according to claim 50, wherein said first oligonucleotide is between about 10 mer to 40 mer.

52. The method according to claim 51, wherein said first oligonucleotide is about 28 mer.

53. The method according to claim 31, wherein said second oligonucleotide is up to 100 mer.

54. The method according to claim 53, wherein said second oligonucleotide is between about 10 mer to 20 mer.

55. The method according to claim 54, wherein said second oligonucleotide is about 14 mer.

56. The method according to claim 31, further comprising the step of adding to said hybridization reaction mixture a terminating solution.

57. The method according to claim 56, wherein said terminating solution comprises 80% formamide, 15 mM tris(hydroxymethyl)aminomethane (TRIS-HCl), pH 7.6, 1 mM EDTA, 0.1% w/v bromophenol blue and 0.1% w/v xylene cyanole FF.

58. The method according to claim 56, wherein 100 μl of said terminating solution is added to said reaction mixture.

59. The method according to claim 32, wherein said nucleic acid target sequence is HPV 16.

60. The method according to claim 31, wherein said detecting step (e) comprises electrophoresing said reaction mixture and autoradiographing said electrophoresed reaction mixture.

61. A method for detecting the presence of a nucleic acid sequence which contains a scissile linkage that is cleavable by a cleaving enzyme in a biological sample, said method comprising the steps of:
(a) hybridizing a target molecule having a scissile linkage to a labelled first oligonucleotide probe that has a complementary sequence to said target and a detectable marker to provide a probe:target duplex;
(b) cleaving said duplex at the scissile linkage;
(c) adding a second oligonucleotide that reconstitutes the cleaved scissile linkage on the target molecule;
(d) recycling the reconstituted target molecule; and
(e) detecting said cleaved first oligonucleotide probe.

62. The method according to claim 61, wherein said target molecule comprises a single-stranded DNA sequence.

63. The method according to claim 62, wherein said first oligonucleotide comprises a single-stranded DNA sequence.

64. The method according to claim 62, wherein said second oligonucleotide comprises a single-stranded DNA sequence.

65. The method according to claim 61, wherein said cleaving step (b) is carried out with a restriction enzyme.

66. The method according to claim 61, wherein said target molecule is single-stranded.

67. The method according to claim 61, wherein said hybridization is carried out at a temperature to enhance the efficiency of said cleaving enzyme and the hybridization of the oligonucleotides.

68. The method according to claim 67, wherein said hybridization is carried out at 37° C.

69. The method according to claim 67, wherein said hybridization is carried out at 32° C.

70. The method according to claim 67, wherein said hybridization is carried out between 1 to 4 hours.

71. The method according to claim 70, wherein said hybridization is carried out for about 2 hours.

72. The method according to claim 61, wherein said cleaving step (b) is further carried out in a buffering system.

73. The method according to claim 72, wherein said system comprises a $MgCl_2$, NaCl, tris(hydroxymethyl)aminomethane-hydrochloride (TRIS-HCl), dithiothreitol (DTT) and bovine standard albumin (BSA).

74. The method according to claim 73, wherein said buffering system comprises 100 mM NaCl, 10 mM tris(hydroxymethyl)aminomethane-hydrochloride (TRIS-HCl), pH7.7, 10 mM $MgCl_2$, 1 mM DTT and 100 $\mu$g/ml BSA.

75. The method according to claim 61, wherein said detectable marker in said first oligonucleotide is a radioactive marker.

76. The method according to claim 75, wherein said radioactive marker is selected from the group consisting of $^{32}P$, $^{3}H$, $^{14}C$ and $^{35}S$.

77. The method according to claim 76, wherein said radioactive marker is $^{32}P$.

78. The method according to claim 61, wherein said detectable marker in said first oligonucleotide is an enzyme marker.

79. The method according to claim 61, wherein said detectable marker in said first oligonucleotide is a ligand which can serve as a specific binding pair member to a labeled compound selected from the group consisting of an antibody, fluorescer, chemiluminescer, enzymes, biotin and mixtures thereof.

80. The method according to claim 61, wherein said first oligonucleotide is up to 100 mer.

81. The method according to claim 80, wherein said first oligonucleotide is between about 10 mer to 40 mer.

82. The method according to claim 81, wherein said first oligonucleotide is about 28 mer.

83. The method according to claim 61, wherein said second oligonucleotide is up to 100 mer.

84. The method according to claim 83, wherein said second oligonucleotide is between about 10 mer to 20 mer.

85. The method according to claim 84, wherein said second oligonucleotide is about 14 mer.

86. The method according to claim 61, further comprising the step of adding to said hybridization reaction mixture a terminating solution.

87. The method according to claim 86, wherein said terminating solution comprises 80% formamide, 15 mM tris(hydroxymethyl)aminomethane-hydrochloride (TRIS-HCl), pH 7.6, 1 mM EDTA, 0.1% w/v bromophenol blue and 0.1% w/v xylene, cyanole FF.

88. The method according to claim 87, wherein 100 $\mu$l of said terminating solution is added to said reaction mixture.

89. The method according to claim 62, wherein said nucleic acid target sequence is HPV 16.

90. The method according to claim 61, wherein said detecting step (e) comprises electrophoresing said reaction mixture and autoradiographing said electrophoresed reaction mixture.

91. The method according to claim 5, wherein said restriction enzyme is selected from the group consisting of Aat II, Acc I, Acc III, Aha II, Alu I, Acc I, Apa I, ApaL I, Ava I, Val I, Bam HI, Bcl I, Bgl I, BssH II, BstE II, Cla I, Dra I, Eco52 I, Eco RI, EcoR II, EcoR V, Fsp I, Hae III, Hha I, Hind III, Hpa I, Kpn I, Ksp I, Nci I, Mst II, Nae I, Pst I, Puv I, and Xba I.

92. The method according to claim 35, wherein said restriction enzyme is selected from the group consisting of Aat II, Acc I, Acc III, Aha II, Alu I, Aoc I, Apa I, ApaL I, Ava I, Bal I, Bam HI, Bcl I, Bgl I, BssH II, BstE II, Cla I, Dra I, Eco52 I, Eco RI, EcoR II, EcoR V, Fsp I, Hae III, Hha I, Hind III, Hpa I, Kpn I, Ksp I, Nci I, Mst II, Nae I, Pst I, Puv I, and Xba I.

93. The method according to claim 92, wherein said restriction enzyme is Eco RI.

94. The method according to claim 92, wherein said restriction enzyme is Pst I.

95. The method according to claim 65, wherein said restriction enzyme is selected from the group consisting of Aat II, Acc I, Acc III, Aha II, Alu I, Acc I, Apa I, ApaL I, Ava I, Bal I, Bam HI, Bcl I, Bgl I, BssH II, BstE II, Cla I, Dra I, Eco52 I, Eco RI, EcoR II, EcoR V, Fsp I, Hae III, Hha I, Hind III, Hpa I, Kpn I, Ksp I, Nci I, Mst II, Nae I, Pst I, Puv I, and Xba I.

96. The method according to claim 95, wherein said restriction enzyme is Eco RI.

97. The method according to claim 95, wherein said restriction enzyme is Pst I.

98. The method according to claim 29, wherein said first oligonucleotide has the sequence:

5'ACC ATG GCT GAT CCT GCA GGT ACC AAT G3'.

99. The method according to claim 29, wherein said second oligonucleotide has the sequence:

5'GGA TCA GCC ATG GT3'.

100. The method according to claim 59, wherein said first oligonucleotide has the sequence:

5'ACC ATG GCT GAT CCT GCA GGT ACC AAT G3'.

101. The method according to claim 59, wherein said second oligonucleotide has the sequence:

5'GGA TCA GCC ATG GT3'.

102. The method according to claim 89, wherein said first oligonucleotide has the sequence:

5'ACC ATG GCT GAT CCT GCA GGT ACC AAT G3'.

103. The method according to claim 89, wherein said second oligonucleotide has the sequence:

5'GGA TCA GCC ATG GT3'.

* * * * *